United States Patent

Sunagawa et al.

[11] 4,224,344
[45] Sep. 23, 1980

[54] ORGANIC TRICYCLIC COMPOUNDS

[75] Inventors: Makoto Sunagawa; Hiromi Sato; Junki Katsube, all of Toyonaka; Hisao Yamamoto, Kobe, all of Japan

[73] Assignee: Sumitomo Chemical Company, Limited, Osaka, Japan

[21] Appl. No.: 639,974

[22] Filed: Dec. 11, 1975

[30] Foreign Application Priority Data

Dec. 13, 1974 [JP] Japan .................................. 49/143734
Dec. 27, 1974 [JP] Japan .................................. 49/2909

[51] Int. Cl.² .......................... C07C 87/28; A01N 9/24
[52] U.S. Cl. .................................. 424/330; 260/349;
260/456 P; 260/465 R; 260/465 B; 260/501.1;
260/544 P; 260/557 R; 260/558 R; 260/558 P;
260/561 N; 260/566 A; 260/566 F; 260/571;
260/570.9; 260/570.8 TC; 424/246; 424/248.4;
424/267; 424/274; 424/316; 544/59; 544/106;
546/203; 560/102; 562/418; 562/499; 568/715;
568/439

[58] Field of Search ................... 260/570.8 TC, 570.9,
260/501.1; 424/316, 332

[56] References Cited

U.S. PATENT DOCUMENTS

| | | | |
|---|---|---|---|
| 3,399,201 | 8/1968 | Schmidt et al. | 260/570.8 X |
| 3,622,630 | 11/1971 | Craig et al. | 260/570.8 |
| 3,708,525 | 1/1973 | Christy | 260/570.6 X |
| 3,862,131 | 1/1975 | Beck et al. | 260/570.8 X |

OTHER PUBLICATIONS

Chenier et al., "Journal Organic Chemistry", vol. 38, pp. 4350–4352 (1973).
Burger, "Medicinal Chemistry", 2nd Ed., pp. 82–83 (1960).

Primary Examiner—Robert V. Hines
Attorney, Agent, or Firm—Birch, Stewart, Kolasch & Birch

[57] ABSTRACT

Novel 9-aminoalkyl-methanoanthracenes of the formula:

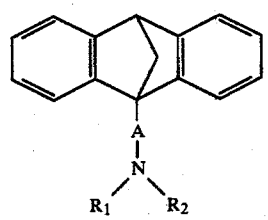

wherein A is $C_1$–$C_4$ alkylene or $C_3$–$C_4$ alkenylene and $R_1$ and $R_2$ are each hydrogen, $C_1$–$C_4$ alkyl, $C_3$–$C_4$ alkenyl, $C_3$–$C_4$ alkynyl, $C_3$–$C_6$ cycloalkyl($C_1$–$C_3$)alkyl, ar(-$C_1$–$C_3$)alkyl or polyhalo($C_2$–$C_4$)alkyl or, when taken together with the adjacent nitrogen atom, they may form a 5 to 7-membered nitrogen-containing heterocyclic ring which may contain an additional hetero atom, and their non-toxic salts, which are useful as antianxiety, anti-depressant, major tranquilizer, anti-histamine and anti-allergy drugs and can be prepared through a novel key intermediate, i.e., 9-formyl-9,10-dihydro-9,10-methanoanthracene, by various methods.

10 Claims, No Drawings

ORGANIC TRICYCLIC COMPOUNDS

The present invention relates to novel organic tricyclic compounds and their production and use. More particularly, it relates to 9-aminoalkyl-9,10-dihydro-9,10-methoanoanthracene derivatives and non-toxic pharmaceutically acceptable salts thereof, to a pharmaceutical composition containing at least one of the 9-aminoalkyl-9,10-dihydro-9,10-methanoanthracene derivatives and their non-toxic pharmaceutically acceptable salts as an active ingredient, to a process for preparing the 9-aminoalkyl-9,10-dihydro-9,10-methanoanthracene derivatives and their salts, and to a use of the 9-aminoalkyl-9,10-dihydro-9,10-methanoanthracene derivatives and their salts. It also relates to 9-formyl-9,10-dihydro-9,10-methanoanthracene, which is a key intermediate for production of the 9-aminoalkyl-9,10-dihydro-9,10-methanoanthracene derivatives, and to a process for its production.

The 9,10-dihydro-9,10-methanoanthracene skeleton itself has been known since 1920, and a few chemical studies have been done on 9,10-dihydro-9,10-methanoanthracene derivatives, but no report has appeared either on the synthesis of 9-aminoalkyl-9,10-dihydro-9,10-methanoanthracene derivatives or on pharmacological studies on 9,10-dihydro-9,10-methanoanthracene derivatives.

It has now been found that novel 9-aminoalkyl-9,10-dihydro-9,10-methanoanthracene derivatives of the following formula [I] and their non-toxic pharmaceutically acceptable salts characteristically have various pharmaceutical properties:

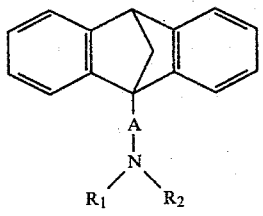

wherein A is $C_1-C_4$ alkylene or $C_3-C_4$ alkenylene and $R_1$ and $R_2$ are each hydrogen, $C_1-C_4$ alkyl, $C_3-C_4$ alkenyl, $C_3-C_4$ alkynyl, $C_3-C_6$ cycloalkyl($C_1-C_3$)alkyl, ar(-$C_1-C_3$)alkyl or polyhalo($C_2-C_4$)alkyl or, when taken together with the adjacent nitrogen atom, they represent a 5 to 7-membered nitrogen-containing heterocyclic ring which may contain an additional hetero atom.

In the above significances, the term "$C_1-C_4$ alkylene" means a straight or branched alkylene group having one to four carbon atoms (e.g. methylene, ethylene, propylene, butylene, 1-methylethylene, 1-methylpropylene, 2-methylpropylene). The term "$C_3-C_4$ alkenylene" includes specifically 1-propenylene, 1-butenylene, 2-butenylene, 1-methyl-1-propenylene and 2-methyl-1-propenylene, of which the numberings are started from the carbon atom linked to the 9,10-dihydro-9,10-methanoanthracene skeleton. The term "$C_1-C_4$ alkyl" means a straight or branched alkyl group having one to four carbon atoms (e.g. methyl, ethyl, n-propyl, isopropyl, n-butyl, sec.-butyl, isobutyl). The term "$C_3-C_4$ alkenyl" means a straight or branched alkenyl group having three or four carbon atoms such as propenyl or butenyl. The term "$C_3-C_4$ alkynyl" means a straight or branched alkynyl group having three or four carbon atoms such as propargyl. The term "$C_3-C_6$ cycloalkyl(-$C_1-C_3$)alkyl" means a straight or branched alkyl group having one to three carbon atoms and bearing a cycloalkyl group consisting of three to six carbon atoms; for example, cyclopropylmethyl and cyclobutylmethyl. The term "ar($C_1-C_3$)alkyl" means a straight or branched alkyl group having one to three carbon atoms (e.g. methyl, ethyl, propyl) and bearing an aryl group (e.g. phenyl). The term "polyhalo($C_2-C_4$)alkyl" means a straight or branched alkyl group having two to four carbon atoms and bearing two or more halogen atoms; for example, trifluoroethyl, trichloroethyl and trifluoropropyl. As the 5 to 7-membered nitrogen-containing heterocyclic ring, there are exemplified pyrrolidino, piperidino, morpholino and thiomorpholino.

The non-toxic pharmaceutically acceptable salts of the 9-aminoalkyl-9,10-dihydro-9,10-methanoanthracene derivatives [I] may include organic and inorganic acid-addition salts thereof, for example, hydrochloride, hydrobromide, acetate, oxalate, citrate, tartrate, succinate, fumarate and lactate.

The 9-aminoalkyl-9,10-dihydro-9,10-methanoanthracene derivatives (hereinafter referred to as "9-aminoalkylmethanoanthracene derivatives") [I] are characterized by the aminoalkyl side chain present at the 9-position of the 9,10-dihydro-9,10-methanoanthracene skeleton.

Although many dibenzotricyclic compounds have been known and some of them are now used clinically as medicines, especially as psychotropic drugs, any dibenzotricyclic compound having a 9,10-dihydro-9,10-methanoanthracene ring as the dibenzotricyclic skeleton has not been employed for such purpose. The entry to the 9-aminoalkyl-methanoanthracene derivatives [I] could be achieved by the success in synthesizing the key intermediate: 9-formyl-9,10-dihydro-9,10-methanoanthracene of the formula:

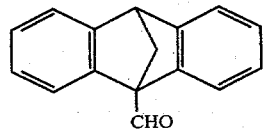

The 9-aminoalkyl-methanoanthracene derivatives [I] are novel and characteristically exhibit a wide variety of valuable pharmacological activities, especially on the central nervous system and autonomic nervous system. More particularly, the 9-aminoalkyl-methanoanthracene derivatives [I] wherein A is methylene which may be substituted with alkyl having one to three carbon atoms, show potentiating action of hexabarbital anesthesia, hypothermia, ptosis and muscle relaxant activity and also anti-tetrabenazine activity. Thus, they are useful as anti-anxiety drugs, anti-depressant drugs and also as major tranquilizers.

The 9-aminoalkyl-methanoanthracene derivatives [I] wherein A is ethylene which may be substituted with alkyl having one or two carbon atoms show potent anti-histamine, anti-collinergic and anti-serotonin activities. They also show anti-tetrabenazine activity. Thus, they are useful as anti-histamine drugs and anti-allergy drugs.

The 9-aminoalkyl-methanoanthracene derivatives [I] wherein A represents $C_3-C_4$ alkylene or $C_3-C_4$ alkenylene show potent anti-tetrabenazine activity. They also show norepinephrine-potentiating action, and anti-reserpine, anti-histamine, anti-collinergic and anti-serotonin activities. Further, their acute toxicity and acute cardio-toxicity have been found to be weak. Thus, they are useful as anti-depressants and anti-histamine drugs.

In any case, the 9-aminoalkyl-methanoanthracene derivatives of the formula [I] all possess anti-tetrabenazine, anti-collinergic, anti-histamine, anti-serotonin and sedative activities in some degrees.

As an anti-anxiety drug, the compounds [I] wherein $R_1$ is $C_1$–$C_2$ alkyl, $R_2$ is hyrogen or $C_1$–$C_2$ alkyl and A is methylene are preferred. As an anti-histamine or antiallergy drug, the compounds [I] wherein $R_1$ is $C_1$–$C_2$ alkyl, $R_2$ is hydrogen or $C_1$–$C_2$ alkyl and A is ethylene are preferred. As an anti-depressant drug, the compounds [I] wherein A is propylene or propenylene are preferred. Particularly preferred are the compounds of the formula [I] wherein $R_1$ and $R_2$ are each independently hydrogen or $C_1$–$C_2$ alkyl and A is propylene or propenylene. The most preferred are those wherein A is propylene, $R_1$ is hydrogen or methyl and $R_2$ is methyl.

The 9-aminoalkyl-methanoanthracene derivatives [I] and their non-toxic pharmaceutically acceptable salts can be administered orally or parenterally at a dosage of generally 5–500 mg/human body, preferably 25–500 mg/human body (about 60 kg of body weight/day) in the form of conventional pharmaceutical preparations.

For instance, they can be administered in the form of conventional solid pharmaceutical preparations (e.g. powders, granules, tablets, capsules) or in the form of conventional liquid pharmaceutical preparations (e.g. suspensions, emulsions, solutions). Such preparations can be prepared by incorporating the 9-aminoalkyl-methanoanthracene derivatives [I] or their non-toxic pharmaceutically acceptable salts either alone or in combination with suitable adjuvants (e.g. starch, lactose, talc) in the conventional manner.

The 9-aminoalkyl-methanoanthracene derivatives [I] can be produced from 9-formyl-9,10-dihydro-9,10-methanoanthracene [II], practically through its suitable derivative(s). Some typical examples of their production methods are shown below:

Method (a)

The 9-aminoalkyl-methanoanthracene compound of the formula:

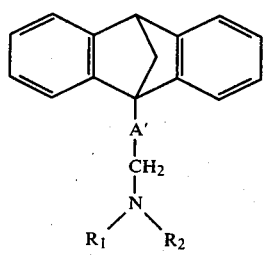

[Ia]

wherein $R_1$ and $R_2$ are each as defined above and A' is a direct linkage, $C_1$–$C_3$ alkylene or $C_2$–$C_3$ alkenylene can be prepared from the corresponding compound of the formula:

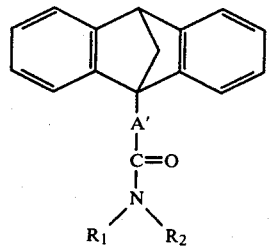

[III]

wherein A', $R_1$ and $R_2$ are each as defined above, by reduction of the latter.

For the reduction, a reducing agent such as an alkali metal in an alcoholic solvent, a metal hydride or the like can be preferably employed. An electrolytic reduction can also be used for the purpose.

It is especially preferable to use a metal hydride such as lithium aluminum hydride, sodium aluminum diethyl dihydride and sodium bis(2-methoxyethoxy)aluminum hydride in an inert organic solvent such as ethers (e.g. diethyl ether, diisopropyl ether, tetrahydrofuran, dioxane, ethylene glycol dimethyl ether), aliphatic hydrocarbons (e.g. heptane, hexane, cyclohexane), aromatic hydrocarbons (e.g. benzene, toluene) or mixtures thereof. The temperature for the treatment in this case may be varied from ice-cooling to the refluxing temperature of the reduction system.

Sodium borohydride is another example of practically utilizable metal hydrides as the reducing agent, particularly when used in the presence of a salt such as aluminum chloride or on activation of the carboxamide group in the compound [III] with triethyloxonium fluoroborate or the like. Diborane is a further example of metal hydrides efficient as the reducing agent.

Method (b)

The 9-aminoalkyl-methanoanthracene compound [I] can be also prepared by reacting the corresponding compound of the formula:

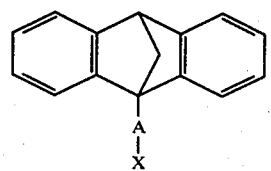

[IV]

wherein A is as defined above and X is a conventional leaving group such as halogen (e.g. chlorine, bromine, iodine) or sulfonyloxy (e.g. methanesulfonyloxy, p-toluenesulfonyloxy, trichloromethanesulfonyloxy) with an amine of the formula:

[V]

wherein $R_1$ and $R_2$ are each as defined above in the presence or absence of an inert solvent such as ethers (e.g. diethyl ether, diisopropyl ether, tetrahydrofuran, dioxane, ethylene glycol dimethyl ether), alcohols (e.g. methanol, ethanol, isopropanol), aromatic hydrocarbons (e.g. benzene, toluene), dimethylsulfoxide, dimethylformamide or pyridine in the presence or absence of a basic binding agent. Examples of the basic binding agent are amines (e.g. pyridine, picoline, triethylamine, dimethylaniline), metal hydrides (e.g. sodium hydride), metal alkoxides (e.g. sodium methoxide, sodium ethoxide, potassium t-butoxide), metal carbonates (e.g. sodium carbonate, potassium carbonate), metal bicarbonates (e.g. sodium bicarbonate), sodium amide, etc. The reaction temperature may be varied from ice-cooling to the refluxing temperature of the reaction system in a closed or open system.

Method (c)

The 9-aminoalkyl-methanoanthracene compound [Ia] can be prepared by the condensation-reduction of the corresponding compound of the formula:

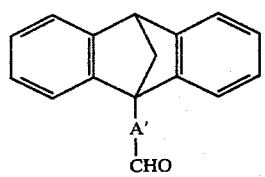

[VI]

wherein A' is as defined above with the amine [V].

The condensation-reduction can be accomplished by known methods. For instance, the usual procedure of the Leuckart-Wallach reaction using formic acid may be adopted [Organic Reactions, Vol. 5, p. 301, John Wiley & Sons, Inc.]. That is, the compound [VI] is added to an amineformate of the amine [V] or a mixture of the amine [V] and formic acid, and the reaction is effected at a temperature from room temperature to 250° C. This reaction may also be carried out in the presence of an inert solvent such as benzene, toluene, nitrobenzene, tetrahydrofuran or dioxane.

The condensation-reduction may be also performed by the hydrogenation procedure of a mixture of the compound [VI] and the amine [V] over a catalyst such as Raney nickel, platinum oxide or palladium in the presence or absence of an inert solvent. The pressure on hydrogenation may be varied from atmospheric pressure to an elevated pressure. A condensing agent such as sodium acetate can be used in the treatment.

Further, the condensation-reduction may be performed by using the sodium-alcohol or zinc acid or alkali method. An inert solvent such as alcohols (e.g. methanol, ethanol, isopropanol), liquid ammonia, acetic acid or ethers (e.g. diethyl ether, dioxane, diisopropyl ether, tetrahydrofuran) is utilizable.

Furthermore, the condensation-reduction may be performed by the reduction of the Schiff base or enamine prepared from the compound [VI] and the amine [V] in a conventional procedure. The reduction may be performed by the catalytic hydrogenation procedure as described above, or by using a reducing agent such as sodium borohydride, diborane, lithium aluminum hydride, sodium aluminum diethyl dihydride, sodium borocyanohydride or sodium bis(2-methoxyethoxy)aluminum hydride in an inert solvent such as methanol, ethanol, isopropanol, n-butanol, t-butanol, benzene, toluene, diethyl ether, diisopropyl ether, dioxane or tetrahydrofuran. The temperature in this case may be varied from −10° C. to the refluxing temperature of the reduction system.

Method (d)

The 9-aminoalkyl-methanoanthracene compound of the formula:

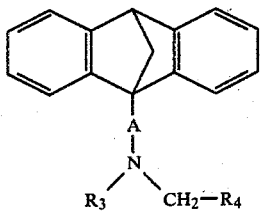

[Ib]

wherein A is as defined above, $R_3$ is hydrogen, $C_1$–$C_4$ alkyl, $C_3$–$C_4$ alkenyl, $C_3$–$C_6$ cycloalkyl($C_1$–$C_3$)alkyl, ar($C_1$–$C_3$)alkyl or polyhalo($C_2$–$C_4$)alkyl and $R_4$ is hydrogen, $C_1$–$C_3$ alkyl, $C_2$–$C_3$ alkenyl, aryl or $C_3$–$C_6$ cycloalkyl can be prepared from the corresponding compound of the formula:

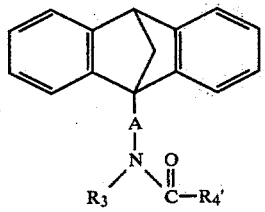

[VII]

wherein A and $R_3$ are each as defined above and $R_4'$ is hydrogen, $C_1$–$C_3$ alkyl, $C_2$–$C_3$ alkenyl, aryl, $C_3$–$C_6$ cycloalkyl, or $C_1$–$C_4$ alkoxy by reduction. The reduction may be performed by the same procedure as mentioned above with respect to the reduction of the compound [III].

Method (e)

The formula 9-aminoalkyl-methanoanthracene compound of the formula:

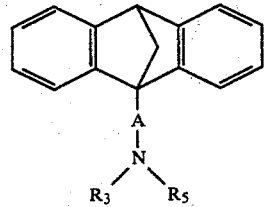

[Ic]

wherein A and $R_3$ are each as defined above and $R_5$ is $C_1$–$C_4$ alkyl, $C_3$–$C_4$ alkenyl, $C_3$–$C_4$ alkynyl, $C_3$–$C_6$ cycloalkyl($C_1$–$C_3$)alkyl, ar($C_1$–$C_3$)alkyl or polyhalo($C_2$–$C_4$)alkyl can be prepared by reacting the corresponding compound of the formula:

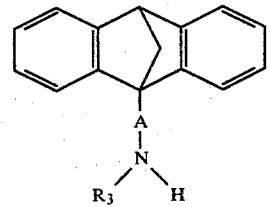

[Id]

wherein A and $R_3$ are each as defined above with a compound of the formula:

$R_5\text{-}X$ [VIII]

wherein $R_5$ and X are each as defined above by the same procedure as mentioned above with respect to the reaction of the compound [IV] with the amine [V].

When the compound [Id] wherein $R_3$ is hydrogen is used, the 9-aminoalkyl-methanoanthracene compound of the formula:

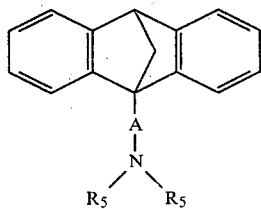

[Ie]

wherein A and $R_5$ are each as defined above can be obtained by reacting the compound [Id] with not less than 2 molar amount of the compound [VIII] in the same procedure.

Method (f)

The 9-aminoalkyl-methanoanthracene compound [Id] can be prepared from the corresponding compound [VII] by hydrolysis. The hydrolysis may be accomplished by a conventional condition under which amide and urethane derivatives are hydrolyzed; for instance, by treatment with an alkali (e.g. potassium hydroxide, sodium hydroxide) or a mineral acid (e.g. hydrochloric acid, hydrobromic acid, sulfuric acid) in an inert solvent such as water, alcohols (e.g. methanol, ethanol, isopropanol, t-butanol, n-butanol, ethylene glycol), ethers (e.g. diethyl ether, tetrahydrofuran, dioxane, ethylene glycol dimethyl ether) or aromatic hydrocarbons (e.g. benzene, toluene). The temperature for the treatment may be varied from ice-cooling to the refluxing temperature of the reaction system.

Method (g)

The 9-aminoalkyl-methanoanthracene compound [Ib] can be prepared by reacting the corresponding compound [Id] with an aldehyde of the formula:

$R_4\text{—CHO}$ [IX]

wherein $R_4$ is defined above by reductive amination. The reductive amination may be performed by the procedure as mentioned above with respect to the condensation-reduction of the compound [VI] with the amine [V].

When the compound [Id] wherein $R_3$ is hydrogen is used, the 9-aminoalkyl-methanoanthracene compound [If] of the formula:

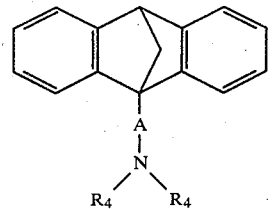

[If]

wherein A and $R_4$ are each as defined above can be obtained by reacting the compound [Id] with not less than 2 molar amount of the compound [IX] in the same procedure.

Method (h)

The 9-aminoalkyl-methanoanthracene compound of the formula:

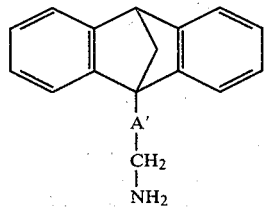

[Ig]

wherein A' is as defined above can be prepared from the corresponding compound of the formula:

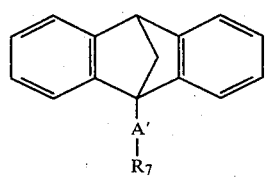

[X]

wherein A' is as defined above and $R_7$ is a nitrile (—C≡N) group or a carbaldehyde oxime (—CH=NOH) group by reduction. The reduction can be accomplished by the procedure as mentioned above with respect to the reduction of the compound [III], or by the catalytic hydrogenation procedure as mentioned in Method (c).

The 9-aminoalkyl-methanoanthracene compound [I] of the invention thus produced may be separated from the reaction mixture and purified by conventional procedures.

The 9-aminoalkyl-methanoanthracene compound [I] may be converted into its salts by conventional procedures, and reconversion from the salts to the original free base may be also carried out by conventional procedures.

The key intermediate, i.e. 9-formyl-9,10-dihydro-9,10-methanoanthracene [II], can be prepared from 9-amino-12-hydroxy-9,10-dihydro-9,10-ethanoanthracene of the formula:

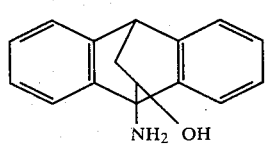

[A]

by rearrangement.

The rearrangement of amines and α-amino-alcohol derivatives by treatment with nitrous acid has been known as the Demjanov rearrangement and Tiffeneu-Demjanov rearrangement [Organic Reactions, Vol. 11, p. 157, John Wiley & Sons, Inc.]. These rearrangement reactions have been applied to the ring-enlargement reaction in most of the reported examples, and only a few examples of the application of the rearrangement reaction to the ring-contraction reaction have been reported. Practically, the rearrangement of a 9,10-ethanoanthracene derivative to 9-formyl-9,10-dihydro-9,10-methanoanthracene has not yet been reported, and it is a new process for the preparation of 9-formyl-9,10-dihydro-9,10-methanoanthracene.

The rearrangement of 9-amino-12-hydroxy-9,10-dihydro-9,10-ethanoanthracene to 9-formyl-9,10-dihydro-9,10-methanoanthracene can be performed by treatment with nitrous acid. That is, 9-amino-12-hydroxy-9,10-dihydro-9,10-ethanoanthracene is treated with nitrous acid or a metal nitrite such as sodium nitrite or potassium nitrite in an acidic medium such as acetic acid, formic acid, hydrochloric acid, hydrobromic acid, sulfuric acid or phosphoric acid or a mixed solution of such acids. An inert solvent such as water, methanol, ethanol, acetone, benzene, toluene, chloroform, dichloroethane, dichloromethane, diethyl ether, ethylene glycol dimethyl ether, tetrahydrofuran, ethyl acetate, dimethylsulfoxide or dimethylformamide or a mixture thereof may be used in the reaction system. The temperature for the treatment in this case may be varied from ice-cooling to the refluxing temperature of the reduction system.

The 9-formyl-9,10-dihydro-9,10-methanoanthracene [II] thus produced can be separated from the reaction mixture and purified by conventional procedures.

The compound [A] (i.e. 9-amino-12-hydroxy-9,10-dihydro-9,10-ethanoanthracene) can be prepared from a compound of the formula:

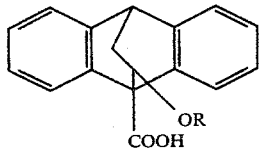

[B]

wherein R is hydrogen or a hydroxyl-protecting group such as acetyl, benzoyl or tetrahydropyranyl through rearrangement such as the Curtius reaction or Hoffman rearrangement and hydrolysis. The rearrangement may be performed, for instance, by the general procedures of the Curtius reaction [Organic Reactions, Vol. 3, p. 337, John Wiley & Sons, Inc.], and the hydrolysis may be effected under the usual hydrolysis conditions for urethane or isocyanate derivatives.

The intermediates for the synthesis of the 9-aminoalkyl-methanoanthracene compounds [I] can be prepared from 9-formyl-9,10-dihydro-9,10-methanoanthracene [II] by using conventional reactions such as oxidation, reduction, hydrolysis, carbon chain extension reaction (substitution, Wittig reaction, Reformatsky reaction, Grignard reaction), etc.

The starting materials for the synthesis of 9-aminomethyl-9,10-dihydro-9,10-methanoanthracene derivatives, for example, may be prepared as follows:

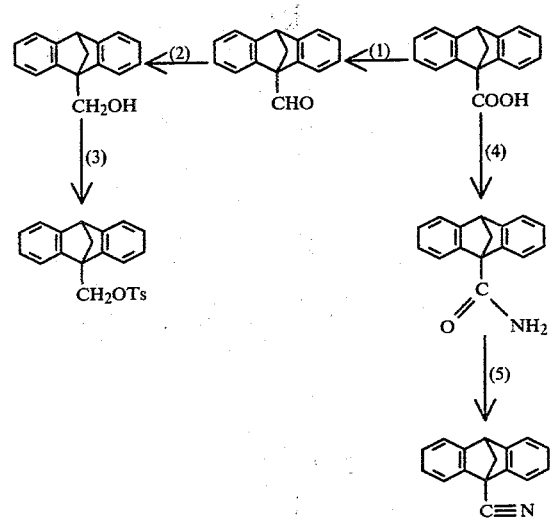

wherein Ts represents a p-toluenesulfonyloxy group; i.e.

(1) 9-Formyl-9,10-dihydro-9,10-methanoanthracene is oxidized to 9,10-dihydro-9,10-methanoanthracene-9-carboxylic acid by treatment with an oxidizing agent such as chromium trioxide or silver oxide in an inert solvent;

(2) 9-Hydroxymethyl-9,10-dihydro-9,10-methanoanthracene is prepared from 9-formyl-9,10-dihydro-9,10-methanoanthracene by treatment with a reducing agent such as sodium borohydride or lithium aluminum hydride in an inert solvent;

(3) 9-Tosyloxymethyl-9,10-dihydro-9,10-methanoanthracene is prepared from 9-hydroxymethyl-9,10-dihydro-9,10-methanoanthracene by treatment with p-toluenesulfonyl chloride in the presence of a base in an inert solvent;

(4) 9,10-Dihydro-9,10-methanoanthracene-9-carboxylic acid is led to the corresponding acid chloride by reacting with thionyl chloride in the presence or absence of an inert solvent, and the acid chloride is converted to 9,10-dihydro-9,10-methanoanthracene-9-carboxamide by reacting with ammonia in a conventional procedure;

(5) Dehydration of 9,10-dihydro-9,10-methanoanthracene-9-carboxamide to 9,10-dihydro-9,10-methanoanthracene-9-carbonitrile is performed by using phosphorus oxychloride in the presence or absence of an inert solvent.

The starting materials for the synthesis of 9-β-aminoethyl-9,10-dihydro-9,10-methanoanthracene derivatives, for example, may be prepared from 9-formyl-9,10-dihydro-9,10-methanoanthracene [II] or its derivatives as follows:

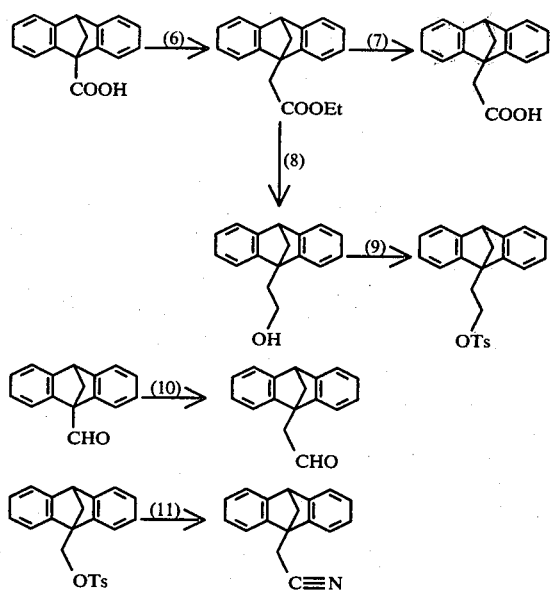

wherein Ts is as defined above; i.e.

(6) [9,10-Dihydro-9,10-methano-9-anthryl]acetic acid ethyl ester is obtained from 9,10-dihydro-9,10-methanoanthracene-9-carboxylic acid by the usual procedure of the Arndt-Eistert synthesis;

(7) [9,10-Dihydro-9,10-methano-9-anthryl]acetic acid is obtained from the corresponding ethyl ester by the usual procedure of hydrolysis;

(8) 9-β-Hydroxyethyl-9,10-dihydro-9,10-methanoanthracene is obtained by reduction of [9,10-dihydro-9,10-methano-9-anthryl]acetic acid ethyl ester using a reducing agent such as lithium aluminum hydride or sodium aluminum diethyl dihydride in an inert solvent;

(9) 9-β-Tosyloxyethyl-9,10-dihydro-9,10-methanoanthracene is obtained by the same manner described above;

(10) [9,10-Dihydro-9,10-methano-9-anthryl]acetaldehyde is obtained from 9-formyl-9,10-dihydro-9,10-methanoanthracene by using the procedure of the Wittig reaction with methoxymethyl triphenylphosphonium chloride and acid hydrolysis;

(11) [9,10-Dihydro-9,10-methano-9-anthryl]acetonitrile can be obtained from 9-tosyloxymethyl-9,10-dihydro-9,10-methanoanthracene by reacting with metal cyanide in an inert solvent.

The starting materials for the synthesis of the 9-γ-aminopropyl and 9-δ-aminobutyl-9,10-dihydro-9,10-methanoanthracene derivatives, for example, may be prepared from 9-formyl-9,10-dihydro-9,10-methanoanthracene [II] as follows:

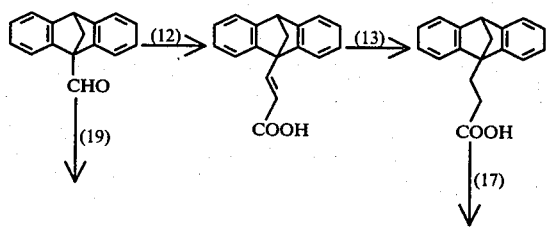

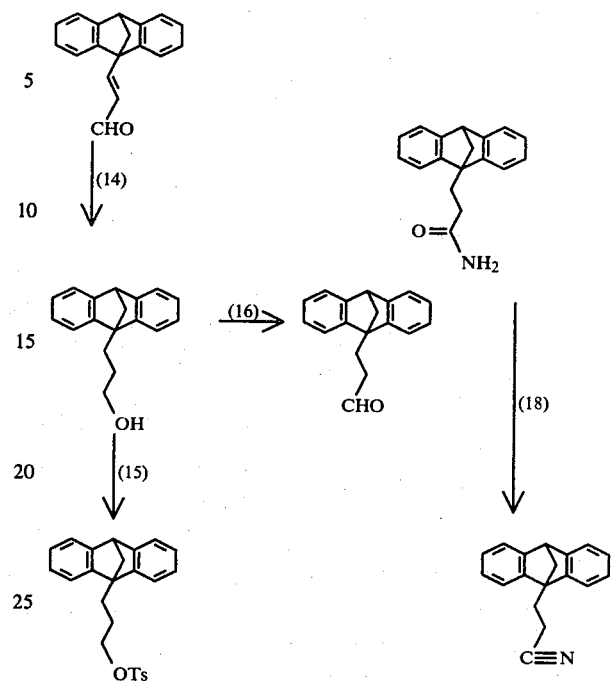

wherein Ts is as defined above; i.e.

(12) β-[9,10-Dihydro-9,10-methano-9-anthryl]-acrylic acid is prepared from 9-formyl-9,10-dihydro-9,10-methanoanthracene by the Wittig reaction procedure with triethyl phosphonoacetate and hydrolysis of the ester function;

(13) β-[9,10-Dihydro-9,10-methano-9-anthryl]-propionic acid is prepared from the corresponding acrylic acid by a conventional hydrogenation procedure;

(14) 9-γ-Hydroxypropyl-9,10-dihydro-9,10-methanoanthracene is prepared from β-[9,10-dihydro-9,10-methano-9-anthryl]propionic acid by treatment with a reducing agent such as lithium aluminum hydride or sodium aluminum diethyl dihydride in an inert solvent;

(15) 9-γ-tosyloxymethyl-9,10-dihydro-9,10-methanoanthracene is prepared from the corresponding alcohol by the procedure as described above;

(16) 9-γ-Hydroxypropyl-9,10-dihydro-9,10-methanoanthracene is oxidized to the corresponding aldehyde by treatment with an oxidizing agent such as CrO₃-pyridine complex in an inert solvent;

(17) & (18) β-[9,10-Dihydro-9,10-methano-9-anthryl]-propionic acid is led to β-[9,10-dihydro-9,10-methanoanthryl]propionitrile by the procedure as described above;

(19) β-[9,10-Dihydro-9,10-methano-9-anthryl]-acrylic aldehyde is prepared from 9-formyl-9,10-dihydro-9,10-methanoanthracene by the Wittig reaction procedure with formylmethylene triphenylphosphoran.

The derivatives of γ-[9,10-dihydro-9,10-methano-9-anthryl]butyric acid can be prepared by the same procedure as described above.

The compound [III] may be prepared from the corresponding carboxylic acid derivative by a conventional procedure with the corresponding amine compound. Another intermediate, i.e. the compound [VII], can be prepared from the compound [Ic] by reacting with the compound of the formula:

R₄COY or R₄CO—O—CO—R₄ wherein R₄ is as defined above and Y is a halogen such as chlorine or bromine in the usual condition for the acylation of an amine compound.

The following examples are given for the purpose of illustration only, and are not intended to limit the invention.

EXAMPLE 1

To a solution of 9-amino-12-hydroxy-9,10-dihydro-9,10-ethanoanthracene (3.0 g) in acetic acid (240 ml) was added a solution of sodium nitrite (6.7 g) in water (120 ml) at 2°–5° C., and the resulting mixture was stirred at the same temperature for 1 hour and at 95°–105° C. for 5 hours. The reaction mixture was diluted with water and extracted with benzene. The benzene layer was washed with water, dried over sodium sulfate and evaporated to dryness to give crude crystals of 9-formyl-9,10-dihydro-9,10-methanoanthracene (2.8 g), which were recrystallized to give colorless crystals (2.45 g). M.P. 99°–100° C. Further, purification by recrystallization gave analytically pure 9-formyl-9,10-dihyfro-9,10-methanoanthracene, M.P. 102.5° C.

EXAMPLE 2

To a solution of 9-amino-12-hydroxy-9,10-dihydro-9,10-ethanoanthracene (50 mg) in conc. hydrochloric acid (2 ml) and water (2 ml) was added a solution of sodium nitrite (112 mg) in water (1.0 ml) at 0° C. The resulting mixture was stirred at 0° C. for 1 hour and at room temperature for 5 hours. The reaction mixture was diluted with water and extracted with benzene. The benzene layer was washed with water, dried over sodium sulfate and evaporated to dryness to give crude crystals of 9-formyl-9,10-dihydro-9,10-methanoanthracene (35 mg).

EXAMPLE 3

A solution of 12-acetoxy-9,10-dihydro-9,10-ethanoanthracene-9-carboxylic acid (1.0 g) in benzene (10.0 ml) and thionyl chloride (4.0 ml) was refluxed for 4 hours. Evaporation of excess thionyl chloride and benzene gave 12-acetoxy-9,10-dihydro-9,10-ethanoanthracene-9-carboxylic acid chloride. The acid chloride was dissolved in dry acetone (25.0 ml), and a solution of sodium azide (0.63 g) in water (1.3 ml) was added thereto while ice cooling. The resulting mixture was stirred while ice cooling for 2 hours. The reaction mixture was diluted with water and extracted with benzene. The benzene extract was washed with water, dried over anhydrous sodium sulfate, refluxed for 2 hours and evaporated to dryness to give 9-isocyanato-12-acetoxy-9,10-dihydro-9,10-ethanoanthracene.

The isocyanate compound was dissolved in ethanol (12.0 ml) and 20% aqueous sodium hydroxide (12.0 ml), and the resulting solution was refluxed for 6 hours. After evaporation of ethanol, the reaction mixture was diluted with water and extracted with ethyl acetate. The ethyl acetate extract was washed with water, dried over anhydrous sodium sulfate and evaporated to dryness to give 9-amino-12-hydroxy-9,10-dihydro-9,10-ethanoanthracene as crystals (0.72 g). M.P. 181°–181.5° C. Recrystallization from benzene gave analytically pure crystals of 9-amino-12-hydroxy-9,10-dihydro-9,10-ethanoanthracene. M.P. 183.5° C.

EXAMPLE 4

A mixture of β-(9,10-dihydro-9,10-methano-9-anthryl)propionic acid monomethylamide (1.0 g) and lithium aluminum hydride (0.5 g) in dioxane was stirred at 50° C. for 2 hours. Excess lithium aluminum hydride was decomposed by addition of water. The reaction mixture was diluted with ethyl acetate, dried over anhydrous sodium sulfate and evaporated to dryness to give 9-γ-methylaminopropyl-9,10-dihydro-9,10-methanoanthracene, which was converted into its hydrochloride. M.P. 247°–249° C. Recrystallization from isopropyl alcohol gave colorless crystals. M.P. 259°–260° C.

The starting amide was prepared as follows:

A solution of β-(9,10-dihydro-9,10-methano-9-anthryl)propionic acid and thionyl chloride in benzene was refluxed for 4 hours. Evaporation of excess thionyl chloride and benzene gave β-(9,10-dihydro-9,10-methano-9-anthryl)-propionic acid chloride, which was dissolved in dry tetrahydrofuran. The solution was added to a 30% aqueous monomethylamine solution at 0°–5° C. The reaction mixture was stirred at 0°–15° C., diluted with water and extracted with ethyl acetate. The ethyl acetate layer was washed with water, dried over anhydrous sodium sulfate and evaporated to dryness to give β-(9,10-dihydro-9,10-methano-9-anthryl)-propionic acid monomethylamide. M.P. 200°–201° C.

EXAMPLE 5

A mixture of 9-γ-chloropropyl-9,10-dihydro-9,10-methanoanthracene (50 mg) and piperidine (0.1 ml) was heated at 100° C. for 3 hours. The reaction mixture was diluted with ethyl acetate, washed with water, dried over anhydrous sodium sulfate and evaporated to dryness to give 9-γ-piperidinopropyl-9,10-dihydro-9,10-methanoanthracene, which was converted into its hydrochloride. M.P. 280°–283° C.

The starting 9-γ-chloropropyl-9,10-dihydro-9,10-methanoanthracene was prepared by reacting 9-γ-hydroxypropyl-9,10-dihydro-9,10-methanoanthracene with thionyl chloride in benzene.

EXAMPLE 6

To a mixture of morpholine (870 mg) and formic acid (460 mg) heated at 60° C. was added β-(9,10-dihydro-9,10-methano-9-anthryl)propionaldehyde (50 mg). The resultant mixture was stirred at 60° C. for 30 minutes and at 80° C. for 1.5 hours. The reaction mixture was diluted with water and extracted with ethyl acetate. The ethyl acetate layer was washed with water, dried over anhydrous sodium sulfate and evaporated to dryness to give 9-γ-morpholinopropyl-9,10-dihydro-9,10-methanoanthracene, which was converted into its hydrochloride. M.P. 173°–176.5° C.

The starting β-(9,10-dihydro-9,10-methano-9-anthryl)propionaldehyde (M.P. 135°–140° C.) was prepared from 9-γ-hydroxypropyl-9,10-dihydro-9,10-methanoanthracene by treating with chromium trioxide-pyridine complex in dichloromethane for 5 minutes at room temperature.

EXAMPLE 7

A solution of β-(9,10-dihydro-9,10-methano-9-anthryl)propionaldehyde (150 mg) and sec.-butylamine (100 mg) in methanol was stirred at −5−0° C. for 30 minutes. To the solution was added sodium borohydride (50 mg), and the resulting mixture was stirred for 2 hours at about 0° C. The reaction mixture was diluted with water and extracted with benzene. The benzene extract was shaken with hydrochloric acid. The acid layer was basified with aqueous ammonia and extracted with ethyl acetate. The ethyl acetate extract was washed with water, dried over anhydrous sodium sulfate and evaporated to dryness to give 9-γ-sec.-butylaminopropyl-9,10-dihydro-9,10-methanoanthracene, which was converted into its hydrochloride. M.P. 216°–219° C.

EXAMPLE 8

A mixture of 9-γ-acetylaminopropyl-9,10-dihydro-9,10-methanoanthracene (70 mg) and lithium aluminum hydride (35 mg) in dioxane (2 ml) was stirred at 40°–50° C. for 9 hours. Excess lithium aluminum hydride was decomposed by addition of water. The reaction mixture was diluted with ethyl acetate, dried over anhydrous sodium sulfate and evaporated to dryness to give 9-γ-ethylaminopropyl-9,10-dihydro-9,10-methanoanthracene, which was converted into its hydrochloride. M.P. 182°–186° C.

EXAMPLE 9

A mixture of 9-γ-methylaminopropyl-9,10-dihydro-9,10-methanoanthracene (40 mg), propargyl bromide (22 mg) and sodium amide (15 mg) in dry benzene was refluxed for 6 hours. The reaction mixture was diluted with benzene, washed with water, dried over anhydrous sodium sulfate and evaporated to dryness. The oily residue was purified over silica gel chromatography to give 9-γ-methylpropargylamino-propyl-9,10-dihydro-9,10-methanoanthracene. M.P. 130°–131° C.

EXAMPLE 10

A mixture of 9-γ-acetylallylaminopropyl-9,10-dihydro-9,10-methanoanthracene (100 mg) in ethanol and 25% aqueous sodium hydroxide was refluxed for 10 hours. The reaction mixture was diluted with water and extracted with ethyl acetate. The ethyl acetate layer was washed with water, dried over anhydrous sodium acetate and evaporated to dryness to give 9-γ-allylaminopropyl-9,10-dihydro-9,10-methanoanthracene, which was converted into its hydrochloride. M.P. 227°–228° C.

EXAMPLE 11

A mixture of 9-γ-aminopropyl-9,10-dihydro-9,10-methanoanthracene (125 mg), 90% formic acid (300 mg) and 37% aqueous formaldehyde solution (0.25 ml) was heated at 90°–100° C. for 8 hours. 4 N Hydrochloric acid was added to the cooled reaction mixture, and the reaction mixture was evaporated to dryness. The residue was diluted with water, basified with aqueous ammonia and extracted with ethyl acetate. The ethyl acetate layer was washed with water, dried over anhydrous sodium sulfate and evaporated to dryness to give 9-γ-dimethylaminopropyl-9,10-dihydro-9,10-methanoanthracene, which was converted into its hydrochloride (M.P. 244°–247° C.). Recrystallization from isopropyl alcohol afforded colorless crystals. M.P. 247°–247.5° C.

EXAMPLE 12

A mixture of β-(9,10-dihydro-9,10-methano-9-anthryl)propionitrile (250 mg) and lithium aluminum hydride (100 mg) in dioxane (12 ml) was stirred at 60° C. for 5 hours. Excess lithium aluminum hydride was decomposed by addition of water. The reaction mixture was diluted with ethyl acetate, dried over anhydrous sodium sulfate and evaporated to dryness to give 9-γ-aminopropyl-9,10-dihydro-9,10-methanoanthracene, which was converted into its hydrochloride. M.P. 275° C. (decomp.).

EXAMPLE 13

To a solution of 9-formyl-9,10-dihydro-9,10-methanoanthracene (3.5 g) in acetone (17 ml) was dropwise added Jones' reagent (5.0 ml) at room temperature. The reaction mixture was stirred at room temperature for 1 hour, diluted with water and extracted with ethyl acetate. The ethyl acetate extract was washed with water, dried over anhydrous sodium sulfate and evaporated to dryness to give 9,10-dihydro-9,10-methanoanthracene-9-carboxylic acid. M.P. 199.5°–200.5° C.

EXAMPLE 14

A solution of 9-formyl-9,10-dihydro-9,10-methanoanthracene (200 mg) and sodium borohydride (60 mg) in methanol (5 ml) was stirred at room temperature for 30 minutes. The reaction mixture was diluted with water and extracted with ethyl acetate. The ethyl acetate layer was washed with water, dried over anhydrous sodium sulfate and evaporated to dryness to give 9-hydroxymethyl-9,10-dihydro-9,10-methanoanthracene. M.P. 165°–166° C.

EXAMPLE 15

A solution of 9,10-dihydro-9,10-methanoanthracene-9-carboxamide (30 mg) and thionyl chloride (0.15 ml) in toluene (1 ml) was refluxed for 18 hours. Evaporation of toluene and excess thionyl chloride gave 9,10-dihydro-9,10-methanoanthracene-9-carbonitrile. M.P. 120°–123° C.

EXAMPLE 16

A solution of 9-aminomethyl-9,10-dihydro-9,10-methanoanthracene (235 mg) and acetic anhydride (217 mg) in ethanol (5.0 ml) was refluxed for 3 hours. The reaction mixture was diluted with water and extracted with ethyl acetate. The ethyl acetate extract was washed with water, aqueous sodium bicarbonate and water, dried over anhydrous sodium sulfate and evaporated to dryness to give 9-acetylaminomethyl-9,10-dihydro-9,10-methanoanthracene. M.P. 184°–185.5° C.

EXAMPLE 17

A solution of 9,10-dihydro-9,10-methanoanthracene-9-carboxylic acid (1.77 g) and thionyl chloride in benzene was refluxed for 4 hours and evaporated to dryness to give the corresponding acid chloride. A solution of the acid chloride in ether was added dropwise to an ethereal diazomethane solution in the presence of triethylamine (1.43 g) at 0° C. The resultant mixture was stirred at 0° C. for 3 hours, filtered and evaporated to dryness to give the corresponding diazomethyl ketone compound. A mixture of the diazomethyl ketone, triethyl amine and silver benzoate in ethanol (60 ml) was refluxed for 13 hours. The reaction mixture was diluted and extracted with ethyl acetate. The ethyl acetate extract was washed with aqueous sodium bicarbonate and water, dried over anhydrous sodium sulfate and evaporated to dryness to give (9,10-dihydro-9,10-methano-9-anthryl)acetic acid ethyl ester. M.P. 81°–84° C.

EXAMPLE 18

A mixture of (9,10-dihydro-9,10-methano-9-anthryl)-acetic acid ethyl ester (125 mg) and lithium aluminum hydride (80 mg) in ether (6 ml) was stirred at room temperature for 1 hour. Excess lithium aluminum hydride was decomposed by addition of water. The reaction mixture was diluted with ethyl acetate, dried over anhydrous sodium sulfate and evaporated to dryness to give crystals of 9-β-hydroxyethyl-9,10-dihydro-9,10-methanoanthracene. M.P. 99°–100.5° C.

EXAMPLE 19

A solution of 9-β-hydroxyethyl-9,10-dihydro-9,10-methanoanthracene (72 mg) and p-toluenesulfonyl chloride (100 mg) in pyridine (1 ml) was stirred overnight. The resulting mixture was diluted with water and extracted with ethyl acetate. The ethyl acetate layer was washed with water, 2 N hydrochloric acid and water, dried over anhydrous sodium sulfate and evaporated to dryness to give crude crystals of 9-β-tosyloxyethyl-9,10-dihydro-9,10-methanoanthracene, which were recrystallized from ethanol to give pure crystals. M.P. 135.5°–138° C.

EXAMPLE 20

Methoxymethyl triphenyl phosphonium chloride (2 mmole) was treated with sodium hydride (2 mmole) in dimethylsulfoxide (6 ml), and 9-formyl-9,10-dihydro-9,10-methanoanthracene was added thereto at room temperature. The resulting mixture was stirred at room temperature for 1 hour and at 50° C. for 3 hours, diluted with water and extracted with benzene. The benzene extract was washed with water, dried over anhydrous sodium sulfate and evaporated to dryness to give an oily compound. The oil was treated with 2 N hydrochloric acid (5 ml) in dioxane (15 ml) at 50° C. for 2 hours. Usual work-up and purification over silica gel chromatography gave (9,10-dihydro-9,10-methano-9-anthryl)-acetaldehyde. I.R. spectra: 2740, 1715, 1440, 1375, 1165, 1135, 1065, 935, 760, 715, 660 cm$^{-1}$.

EXAMPLE 21

A solution of β-(9,10-dihydro-9,10-methano-9-anthryl)propionic acid (0.7 g) and thionyl chloride in benzene was refluxed for 2 hours and evaporated to dryness to give the corresponding acid chloride, which was dissolved in acetone (3.7 ml). A solution of sodium azide (0.52 g) in water was added to the acetone solution while ice cooling. The resulting mixture was stirred at 0° C. for 2 hours. The reaction mixture was diluted with water and extracted with benzene. The benzene layer was washed with water, dried over sodium sulfate and evaporated to dryness to give the corresponding acid azide. A solution of the acid azide in ethanol (7.5 ml) was refluxed for 10 hours and evaporated to dryness to give 9-β-ethoxycarbonylaminoethyl-9,10-dihydro-9,10-methanoanthracene. M.P. 122°–123° C.

EXAMPLE 22

A mixture of 9-tosyloxymethyl-9,10-dihydro-9,10-methanoanthracene (188 mg) and potassium cyanate (40 mg) in dimethylformamide (2 ml) was heated at 150° C. for 7 hours. The reaction mixture was diluted with water and extracted with benzene. The benzene extract was washed with water, dried over anhydrous sodium sulfate and evaporated to dryness to give crude crystals of (9,10-dihydro-9,10-methano-9-anthryl)acetonitrile, which was recrystallized from isopropanol to give pure crystals. M.P. 130°–131° C.

EXAMPLE 23

Triethyl phosphonoacetate (2.65 g) in benzene was treated with 50% sodium hydride dispersion in mineral oil (0.66 g), and a solution of 9-formyl-9,10-dihydro-9,10-methanoanthracene (2.0 g) in benzene (20.0 ml) was added thereto at room temperature under nitrogen. The reaction mixture was stirred at room temperature for 5 hours and at 70° C. for 1 hour, diluted with water and extracted with ethyl acetate. The ethyl acetate extract was washed with water, dried over anhydrous sodium sulfate and evaporated to dryness to give β-(9,10-dihydro-9,10-methano-9-anthryl)acrylic acid ethyl ester. A solution of the ethyl ester in methanol (53 ml) and 10% aqueous sodium hydroxide (12 ml) was refluxed for 4 hours. The reaction mixture was diluted with water, acidified with hydrochloric acid and extracted with ethyl acetate. The ethyl acetate extract was washed with water, dried over anhydrous sodium sulfate and evaporated to dryness to give β-(9,10-dihydro-9,10-methano-9-anthryl)acrylic acid. M.P. 219.5°–222° C.

EXAMPLE 24

A mixture of β-(9,10-dihydro-9,10-methano-9-anthryl)acrylic acid (612 mg) and 5% palladium-charcoal (120 mg) in ethanol was stirred under a hydrogen atmosphere at room temperature for 2 hours. The catalyst was removed by filtration, and the solution was evaporated to dryness to give β-(9,10-dihydro-9,10-methano-9-anthryl)propionic acid. M.P. 185°–189° C.

EXAMPLE 25

A solution of 9-formyl-9,10-dihydro-9,10-methanoanthracene (220 mg) and formyl methylene triphenyl phosphoran (1 mmole) in benzene (6 ml) was refluxed for 16 hours. The reaction mixture was washed with water, dried over anhydrous sodium sulfate and evaporated to dryness. The oily residue was purified over silica gel chromatography to give the crystals of β-(9,10-dihydro-9,10-methano-9-anthryl)acrylic aldehyde. M.P. 135°–138° C.

EXAMPLE 26

To a mixture of 9-formyl-9,10-dihydro-9,10-methanoanthracene (110 mg) and β-carboxyethyltriphenylphosphonium chloride (186 mg) in dimethylsulfoxide (2 ml) and tetrahydrofuran (2 ml) was added 65.4% sodium hydride dispersion in mineral oil (37 mg) at 0° C. under nitrogen. The reaction mixture was stirred at 0° C. for 6 hours, diluted with water, acidified with hydrochloric acid and extracted with benzene. The benzene extract was shaken with 2 N aqueous sodium hydroxide. The basic layer was acidified with hydrochloric acid and extracted with ethyl acetate. The ethyl acetate extract was washed with water, dried over anhydrous sodium sulfate and evaporated to dryness to give γ-(9,10-dihydro-9,10-methano-9-anthryl)-β-butenoic acid. M.P. 166°–167° C.

The following compounds were prepared in similar procedures:

9-Aminomethyl-9,10-dihydro-9,10-methanoanthracene hydrochloride, M.P. >300° C.;

9-Methylaminomethyl-9,10-dihydro-9,10-methanoanthracene hydrochloride, M.P. 281.5°–283° C.;

9-Dimethylaminomethyl-9,10-dihydro-9,10-methanoanthracene hydrochloride, M.P. 257°-259° C.;

9-Ethylaminomethyl-9,10-dihydro-9,10-methanoanthracene hydrochloride, M.P. 283°-284° C.;

9-Ethylmethylaminomethyl-9,10-dihydro-9,10-methanoanthracene hydrochloride, M.P. 249.5°-251° C.;

9-Isopropylaminomethyl-9,10-dihydro-9,10-methanoanthracene, M.P. 103°-103.5° C.;

9-sec.-Butylaminomethyl-9,10-dihydro-9,10-methanoanthracene hydrochloride, M.P. 234°-235.5° C.;

9-Isobutylaminomethyl-9,10-dihydro-9,10-methanoanthracene hydrochloride, M.P. 227°-229° C.;

9-Cyclopropylmethylaminomethyl-9,10-dihydro-9,10-methanoanthracene hydrochloride, M.P. 240.5°-243.5° C.;

9-Allylaminomethyl-9,10-dihydro-9,10-methanoanthracene hydrochloride, M.P. 208°-209° C.;

9-Benzylaminomethyl-9,10-dihydro-9,10-methanoanthracene, M.P. 94°-97° C.;

9-Piperidinomethyl-9,10-dihydro-9,10-methanoanthracene, M.P. 114°-115° C.;

9-Morpholinomethyl-9,10-dihydro-9,10-methanoanthracene, M.P. 160°-163° C.;

9-$\beta$-Aminoethyl-9,10-dihydro-9,10-methanoanthracene, M.P. 158°-160° C.;

9-$\beta$-Methylaminoethyl-9,10-dihydro-9,10-methanoanthracene hydrochloride, M.P. 304°-305° C.;

9-$\beta$-Dimethylaminoethyl-9,10-dihydro-9,10-methanoanthracene hydrochloride, M.P. 239°-240.5° C.;

9-$\beta$-Ethylaminoethyl-9,10-dihydro-9,10-methanoanthracene hydrochloride, M.P. 297°-299° C.;

9-$\beta$-Diethylaminoethyl-9,10-dihydro-9,10-methanoanthracene, I.R. spectra: 3065, 1468, 1445, 1380, 1280, 1205, 1155, 1010, 765, 745 cm$^{-1}$;

9-$\beta$-sec.-Butylaminoethyl-9,10-dihydro-9,10-methanoanthracene hydrochloride, M.P. 267°-268° C.;

9-$\beta$-Dicyclopropylmethylaminoethyl-9,10-dihydro-9,10-methanoanthracene hydrochloride, M.P. 137°-140° C.;

9-$\beta$-Allylaminoethyl-9,10-dihydro-9,10-methanoanthracene hydrochloride, M.P. 242°-243° C.;

9-$\beta$-Benzylaminoethyl-9,10-dihydro-9,10-methanoanthracene hydrochloride, M.P. 233°-235° C.;

9-$\beta$-Morpholinoethyl-9,10-dihydro-9,10-methanoanthracene hydrochloride, M.P. 263°-264° C.;

9-$\gamma$-Aminopropyl-9,10-dihydro-9,10-methanoanthracene hydrochloride, M.P. 275° C.;

9-$\gamma$-Methylaminopropyl-9,10-dihydro-9,10-methanoanthracene hydrochloride, M.P. 259°-260° C.;

9-$\gamma$-Methylaminopropenyl-9,10-dihydro-9,10-methanoanthracene hydrochloride, M.P. 244°-246° C.;

9-$\gamma$-Dimethylaminopropyl-9,10-dihydro-9,10-methanoanthracene hydrochloride, M.P. 247°-247.5° C.;

9-$\gamma$-Ethylaminopropyl-9,10-dihydro-9,10-methanoanthracene hydrochloride, M.P. 184°-186° C.;

9-$\gamma$-Ethylmethylaminopropyl-9,10-dihydro-9,10-methanoanthracene oxalate, M.P. 168°-169° C.;

9-$\gamma$-Isopropylaminopropyl-9,10-dihydro-9,10-methanoanthracene hydrochloride, M.P. 255°-256° C.;

9-$\gamma$-Isobutylaminopropyl-9,10-dihydro-9,10-methanoanthracene hydrochloride, M.P. 248°-252° C.;

9-$\gamma$-sec.Butylaminopropyl-9,10-dihydro-9,10-methanoanthracene hydrochloride, M.P. 217°-219° C.;

9-$\gamma$-Benzylcyclopropylmethylaminopropyl-9,10-dihydro-9,10-methanoanthracene hydrochloride, M.P. 207°-211° C.;

9-$\gamma$-Allylaminopropyl-9,10-dihydro-9,10-methanoanthracene hydrochloride, M.P. 226°-228° C.;

9-$\gamma$-Benzylaminopropyl-9,10-dihydro-9,10-methanoanthracene hydrochloride, M.P. 197°-201° C.;

9-$\gamma$-Methylpropargylaminopropyl-9,10-dihydro-9,10-methanoanthracene, M.P. 130°-131° C.;

9-$\gamma$-(2,2,2-Trifluoroethyl)methylaminopropyl-9,10-dihydro-9,10-methanoanthracene hydrochloride, M.P. 170°-172.5° C.;

9-$\gamma$-Piperidinopropyl-9,10-dihydro-9,10-methanoanthracene hydrochloride, M.P. 280°-283° C.;

9-$\gamma$-Pyrrolidinopropyl-9,10-dihydro-9,10-methanoanthracene hydrochloride, M.P. 244°-248° C.;

9-$\gamma$-Morpholinopropyl-9,10-dihydro-9,10-methanoanthracene hydrochloride, M.P. 174°-177° C.;

9-$\delta$-Dimethylaminobutyl-9,10-dihydro-9,10-methanoanthracene hydrochloride, M.P. 201°-202.5° C.;

9-$\delta$-Dimethylamino-$\alpha$-butenyl-9,10-dihydro-9,10-methanoanthracene hydrochloride, M.P. 154.5°-155° C., etc.

The following compounds can be prepared by a similar procedure:

9-Propargylaminomethyl-9,10-dihydro-9,10-methanoanthracene;

9-(2,2,2-Trifluoroethyl)aminomethyl-9,10-dihydro-9,10-methanoanthracene;

9-$\beta$-Propargylaminoethyl-9,10-dihydro-9,10-methanoanthracene;

9-$\beta$-Piperazinoethyl-9,10-dihydro-9,10-methanoanthracene;

9-$\beta$-Methyl-$\gamma$-methylaminopropyl-9,10-dihydro-9,10-methanoanthracene;

9-$\alpha$-Methyl-$\beta$-dimethylaminoethyl-9,10-dihydro-9,10-methanoanthracene, etc.

What is claimed is:

1. A compound of the formula:

wherein A is $C_1$-$C_4$ alkylene or $C_3$-$C_4$ alkenylene and $R_1$ and $R_2$ are each hydrogen, $C_1$-$C_4$ alkyl, $C_3$-$C_4$ alkenyl, $C_3$-$C_4$ alkynyl, $C_3$-$C_6$ cycloalkyl($C_1$-$C_3$)alkyl, ar(-$C_1$-$C_3$)alkyl or polyhalo($C_2$-$C_4$)alkyl or a non-toxic pharmaceutically acceptable salt thereof.

2. A compound according to claim 1, wherein A is methylene, $R_1$ is $C_1$-$C_2$ alkyl and $R_2$ is hydrogen or $C_1$-$C_2$ alkyl.

3. A compound according to claim 1, wherein A is ethylene, $R_1$ is $C_1$-$C_2$ alkyl and $R_2$ is hydrogen or $C_1$-$C_2$ alkyl.

4. A compound according to claim 1, wherein A is propylene or propenylene.

5. A compound according to claim 4, wherein $R_1$ is $C_1$-$C_2$ alkyl and $R_2$ is hydrogen or $C_1$-$C_2$ alkyl.

6. A compound according to claim 1, wherein A is propylene, $R_1$ is methyl and $R_2$ is hydrogen or methyl.

7. 9-γ-Methylaminopropyl-9,10-dihydro-9,10-methanoanthracene and or a non-toxic pharmaceutically acceptable salt.

8. 9-γ-Dimethylaminopropyl-9,10-dihydro-9,10-methanoanthracene and or a non-toxic pharmaceutically acceptable salt.

9. A pharmaceutical composition which comprises as an active ingredient a pharmaceutically effective amount of the compound of claim 1, and a pharmaceutically acceptable adjuvant.

10. A method for treating a patient which comprises administering to said patient a pharmaceutically effective amount of the composition of claim 9.

UNITED STATES PATENT AND TRADEMARK OFFICE
CERTIFICATE OF CORRECTION

PATENT NO. : 4,224,344
DATED : Sept. 23, 1980
INVENTOR(S) : Makoto Sunagawa et al It is certified that error appears in the above-identified patent and that said Letters Patent are hereby corrected as shown below:

In the Section entitled "[30] Foreign Application Priority Data" please add the following Japanese applications thereto:

--     April 4, 1975     Japan     50/41452

July 7, 1975     Japan     50/83871     --

Signed and Sealed this

Twenty-seventh Day of January 1981

[SEAL]

Attest:

RENE D. TEGTMEYER

Attesting Officer     Acting Commissioner of Patents and Trademarks